United States Patent [19]

Slowik

[11] 4,144,759
[45] Mar. 20, 1979

[54] AUTOMATIC PULVERIZED COAL SAMPLER

[76] Inventor: Alfred A. Slowik, 120 Keppler Dr., Johnstown, Pa. 15905

[21] Appl. No.: 851,864

[22] Filed: Nov. 16, 1977

[51] Int. Cl.² .............................................. G01N 1/14
[52] U.S. Cl. .................................................. 73/422 R
[58] Field of Search .......................... 73/421 B, 422 R

[56] References Cited

U.S. PATENT DOCUMENTS

| | | | |
|---|---|---|---|
| 2,370,260 | 2/1945 | Robinson | 73/422 |
| 2,968,948 | 1/1961 | Rose | 73/421 B |
| 3,233,463 | 2/1966 | Kaufmann | 73/421 B |
| 3,241,371 | 3/1966 | Horeth | 73/422 |
| 3,555,910 | 1/1971 | Spence et al. | 73/422 |
| 3,575,055 | 3/1971 | Thornton, Jr. | 73/422 |
| 3,659,461 | 5/1972 | Thompson | 73/422 |
| 3,782,200 | 1/1974 | Maas | 73/422 |
| 3,880,011 | 3/1975 | Johnson | 73/422 |

FOREIGN PATENT DOCUMENTS 190656   1965   U.S.S.R. .................................. 73/422

*Primary Examiner*—S. Clement Swisher
*Attorney, Agent, or Firm*—Stevens, Davis, Miller & Mosher

[57] ABSTRACT

An apparatus for sampling powdered material which is moving along with a flow of gas or air through a large pipe. A probe located in the center of the pipe and facing upstream is connected to a smaller conduit leading to a cyclone separator. When a valve on the conduit is opened periodically, a free flow of gas and powdered material goes through the conduit to a cyclone separator. At the bottom of that separator is a sample-collecting container which can be removed periodically to test the accumulated contents. The valve on the conduit is opened and closed by means of air pressure. Prior to opening of that valve, that same air pressure is used to purge the conduit between the valve and the probe of accumulated powdered material.

9 Claims, 1 Drawing Figure

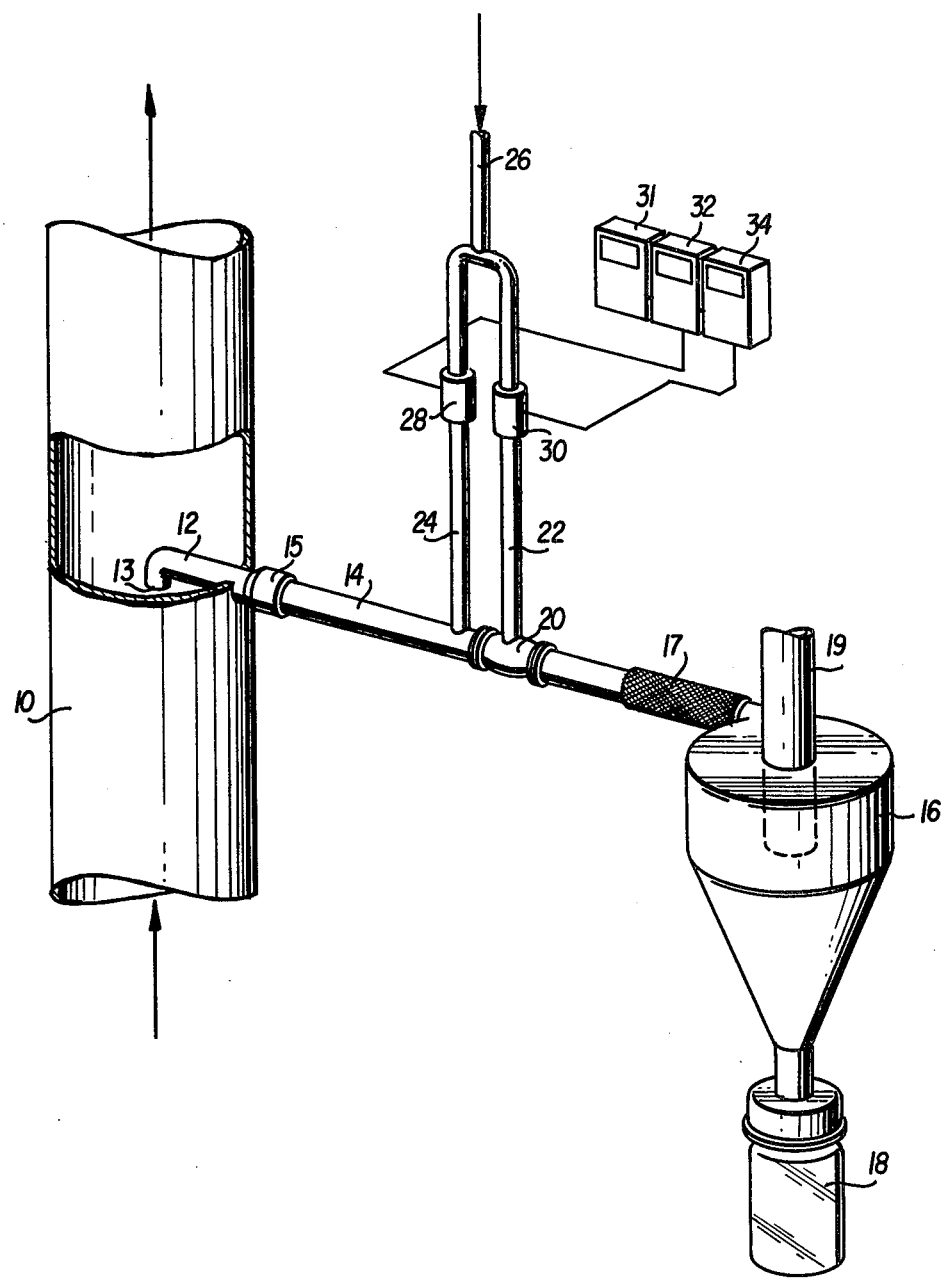

AUTOMATIC PULVERIZED COAL SAMPLER

BACKGROUND OF THE INVENTION

1. Field of the Invention

The present invention relates to automatic sampling of powdered material which is moving through a pipe by means of pressurized gas, such as air, which is also flowing through that pipe. It particularly relates to the sampling of powdered coal, which has been ground in a mill and is being transported, by means of a pipe, to a boiler for burning. The purpose of such sampling is to determine the contents of the coal on an "as burned" basis, particularly to determine the presence of potentially polluting substances such as sulphur. In recent years, the detection of such substances has become very important in order to meet the requirements of the Environmental Protection Agency and corresponding agencies in various states such as the Pennsylvania Department of Environmental Resources.

The present apparatus is assembled and installed so as to provide automatic withdrawal of small sample portions at regular timed intervals in order that a composite sample of the coal being moved through the pipe can be obtained for subsequent analysis.

2. Description of the Prior Art

There is a large body of prior art in the field of sampling apparatus. In this connection, reference is made to U.S. Pat. No. 3,575,055 issued Apr. 13, 1971 in which a portion of material moving downwardly through an inclined pipe is sampled. Another example is use of apparatus having moveable probes such as that shown in U.S. Pat. No. 2,370,260 issued Feb. 27, 1945 or U.S. Pat. No. 3,241,371 issued Mar. 22, 1966.

SUMMARY OF THE INVENTION

The presently disclosed invention comprises an apparatus for automatically sampling solids which are flowing, by means of gas or air pressure through a pipe. A fixed probe extends diametrically into the pipe to approximately the center of it. That probe is connected to a conduit through which the collected sample of material flows, along with part of the gas or air, to a collecting cyclone. The flow through this conduit is not continuous but is interrupted so that a sample is obtained only at periodic intervals. The flow is interrupted preferably by means of a pinch valve which will be described later in greater detail. The powdered material flows from the valve into a cyclone separator where the air or other gas associated with it is separated and vented to the atmosphere. The remaining solid material then drops, by gravity, into the collecting container. Prior to opening the pinch valve for each collection, a burst of clean air is forced in the reverse direction of normal flow through the conduit between the pinch valve and the probe. The purpose of this air is to purge out any powdered material which may have collected since the previous sampling. The operation of the pinch valve and the purge is preferably controlled by solenoid valves which are actuated by electric timers or relays.

BRIEF DESCRIPTION OF THE DRAWING

The annexed drawing sets forth in detail an illustrative view of the present invention, this drawing being a perspective schematic illustration which is not drawn to scale.

DESCRIPTION OF THE PREFERRED EMBODIMENT

The present invention can be readily understood from the following detailed description by reference to the single figure of drawings. In the drawing, powdered material such as coal is carried upward through a pipe 10 toward its destination, such as a boiler, which is located upstream of the pipe and forms no part of this invention. A probe 12 projects diametrically into the pipe 10 and has an open mouth 13 which is perpendicular to the axis of the pipe, that open mouth facing upstream in the pipe so that both the coal particles and the moving air which suspends the particles can freely enter it. The location of the probe mouth 13 has been carefully chosen by experimentation so as to be in a position to receive a representative sample of the particles in the pipe. These experiments have shown that a location approximately in the center of the pipe is preferable. In a typical installation the probe has about a one-half inch inside diameter and thus presents no particular obstruction to the unsampled particles moving through the pipe. As shown in the drawing, the probe has a smooth curve in its bent portion so as to insure free flow of the air and powdered material moving therethrough.

The probe 12 is connected to a conduit 14 by means of a coupling 15 which can be flexible. The other end of the conduit is connected to a cyclone separator 16. The particles move in a circular path to lose their velocity and settle downwardly. The cyclone is preferably funnel-shaped, tapering downwardly toward a collecting container 18 which may be a screw-top Mason jar. A coupling 17, which can be flexible, connects the conduit 14 to the inlet of the cyclone 16. A vent 19 from the top of the cyclone is connected to the atmosphere, perhaps by venting into the negative side of the boiler.

Interposed in conduit 14 is a valve 20. This valve is preferably a so-called pinch valve. Such a valve is normally open, having an internal cylinder made of a flexible material such as rubber. When the space between the flexible cylinder and the outer housing is pressurized, the flexible cylinder is forced inwardly, closing the valve. When such a valve opens, it allows for a very free flow with no obstructions or crevices which would collect or accumulate particles passing therethrough.

A source of constant air pressure (not shown) is connected to air line 26, this line being divided into two other air lines 22 and 24 in which are interposed electrically operated solenoid valves 28 and 30. Valve 30 is preferably a normally open valve, that is, one which will have an open main passage when not energized. When energized, it closes off the flow of air pressure from conduit 26 and vents the pressure from the portion of line 22 between it and the pinch valve so that the rubber cylinder of the pinch valve will, by its own elasticity, place itself in an open position.

Solenoid valve 28 is preferably a normally closed valve, that is, one which is closed when not energized, and when energized will open to connect the source of air pressure directly to conduit 14. The purpose of this connection is to permit a free flow of pressure from the pressure source at about 50 lbs. per square inch into conduit 14 so as to completely blow out any powdered material which may have entered probe 12 or conduit 14 between sampling cycles.

Timer 31 runs continuously, its function being to actuate timer 34 and relay 32 to control the frequency of sampling cycles. When the time for a sampling cycle arrives, timer 31 sends a signal to actuate relay 32.

Relay 32 is then connected to open solenoid valve 28 for a short purge cycle and to then immediately close it.

Relay 32 is in turn connected to timer 34 so that after the open cycle for solenoid valve 28 is completed, it sends a signal to timer 34 so as to start its cycle and cause it to close valve 30, thus cutting off the source of air pressure and permitting the air in line 22 to vent so that pinch valve 20 will open.

When pinch valve 20 is open, there is a complete free flowing open circuit from the mouth of probe 12 to the vent 19 of cyclone 16. Thus air or gas moving upstream in pipe 10, along with the powdered material suspended in it, will move freely through probe 12, through conduit 14 and valve 20 and into cyclone 16. In the cyclone the gas can move freely out of vent 19 while the solid particles travel around the funnel of the cyclone, loose their velocity and drop into container 18. There are, of course, limitations on the length of the conduit 14 so that there is not too great a pressure drop along its length. In one working embodiment conduit 14 has a one inch inside diameter and is about three feet long and there is a pressure head in pipe 10 of about ten inches of water.

In unusual circumstances where the length of conduit 14 must be considerably longer or where the pressure head in pipe 10 is not as great, then it is contemplated that additional flow inducement may be necessary such as by aspirating means or negative pressure applied to vent 19.

In the particular working embodiment mentioned above, the pinch valve is a Miniflex series 2600¾" valve with a pure gum rubber sleeve and a steel body as made by the Red Valve Co. of Carnegie, Pennsylvania; the solenoid valves are type V56DB2100 Skinner solenoid valves; timers 31 and 34 are Tankard series 325 digital setting automatic reset general purpose timers from Automatic Timing & Control Co., King of Prussia, Pennsylvania; relay 32 is a 7012AC Agastat Timing Relay and the cyclone was made by Marine Sheet Metal Works of Erie, Pennsylvania (see instructions for CE Raymond Bowl Mill no. 633, FIG. 11). The probe was shop fabricated from stainless steel with a 90° bend near its far end.

CYCLE OF OPERATION

As previously stated, it is contemplated that this sampling apparatus will operate for only short, periodically spaced intervals, and thus the "normal" position for the system will be one in which pinch valve 20 is closed and there is no powdered material moving through conduit 14. The precise timing of the operating cycle of the sampling mechanism is site dependent, depending upon such factors as coal pipe air pressure and coal density, but the typical cycle is of five minutes duration consisting of a five second purge, a fifteen second sampling interval, and a four minute, forty second wait unit the next purge. Samples are generally collected over a 24-hour period, and then the sampling container is removed and taken to a laboratory for detailed analysis of the content, such as its sulphur.

The cycle of operation of a preferred embodiment of the present apparatus would be as follows: valve 28 is open for five seconds so as to purge conduit 14 and blow out all accumulated powdered material in that conduit and the probe; relay 32 is then actuated by timer 31 and causes valve 28 to close to stop the purge cycle and then relay 32 completes a circuit to timer 34 so that it causes normally open solenoid valve 30 to close, permitting line 22 to vent and pinch valve 20 to open. Gas & particles from coal pipe 10 will then move through conduit 14 to cyclone 16 as previously described; this flow will continue for about 15 seconds, and then timer 34 will cause solenoid valve 30 to open again, exposing pinch valve to air pressure from conduit 26, thus closing it.

The cyle of operation of purge solenoid valve 28 and pinch solenoid valve 30 will be as shown in the following table.

| purge solenoid | pinch solenoid |
| --- | --- |
| closed | open |
| open (5 seconds) | open |
| closed | closed (vent port open) |
| closed | open |

The foregoing, of course, is a description of one preferred embodiment which has been found to be effective at a particular site. It is given by way of illustration only with the scope of this invention being defined by the following claims.

I claim:

1. An apparatus for periodically sampling pulverent material moving by pressurized gas through a pipe by diverting a portion of the gas and pulverent material to freely flow therethrough, said apparatus comprising:
    a probe fixed in relation to the pipe and having an open mouth facing upstream in the pipe at approximately the center of the pipe;
    a cyclone separator connected to said probe by a conduit and having a vent open to the atmosphere and a sample collecting means;
    a quick opening free flowing fluid operated valve in said conduit between the probe and the cyclone, the valve having an outer housing and an internal flexible cylinder within the housing which closes radially inwardly when subjected to fluid pressure by pressurizing the space between the cylinder and the housing;
    an air line connected to said conduit between the valve and the probe to purge pulverent material therefrom;
    control means to open and close said air line and said valve at spaced periodic intervals.

2. The apparatus of claim 1 in which said probe extends radially into the pipe.

3. The apparatus of claim 1 in which the cyclone separator has a conically tapered lower portion.

4. The apparatus of claim 1 in which the valve is pneumatically operated by the same air pressure source as is used for the purge air line.

5. The apparatus of claim 1 in which the fluid operated valve is pneumatically operated and the control means is two solenoid valves, one on said purge air line and one on an air line operating the pneumatic valve, and electric timer means to actuate said solenoid valves.

6. The apparatus of claim 5 in which the electric timer means is two timer switches and a relay which are interconnected.

7. An apparatus for periodically sampling pulverent material moving by pressurized air through a pipe by diverting a portion of the air and pulverent material to flow freely therethrough, said apparatus comprising:

a fixed probe extending radially into the pipe to approximately the center thereof and having an open mouth facing upstream;

a cyclone separator connected to said probe by a conduit, the separator having a vent open to the atmosphere, a sample collecting container at the lower portion thereof;

a pneumatically operated normally open, clog free quick closing pinch valve means in the conduit between the probe and the cyclone, said valve having an outer rigid body and an inner flexible cylindrical sleeve which closes radially inwardly when subjected to fluid pressure by pressurizing the space between the cylinder and the body;

a source of air pressure connected through a first electrically operated valve to said pinch valve;

purge means for said conduit comprising an air line connecting said source of air pressure through a second electrically operated valve to a point on said conduit which is immediately upstream of said pinch valve;

electric switch means connected to open said first and second electrically operated valves at periodic intervals with said second valve being opened slightly prior to the first valve and held open for a short interval to purge the conduit and the second valve being closed substantially simultaneously with the closing of the first valve so that the conduit and the pinch valve cylinder is then open to allow free flow of air and pulverent material into the cyclone separator.

8. A method of obtaining samples at regular intervals over an extended period of time of a pulverent material moving by air pressure through a pipe, said method comprising:

collecting a sample of the air and pulverent material from the pipe by means of a probe positioned centrally therein;

passing said sample air and pulverent material freely through a conduit toward a sample collecting container;

separating the air from said collected sample by passing the air and pulverent material through a cyclone separator, venting the air off through the top of the separator and collecting the pulverent material at the bottom of the separator;

controlling the flow of the collected sample material to the cyclone by means of a fluid operated valve having an outer housing and an internal flexible cylinder;

operating said fluid operated valve by means of fluid pressure from a separate source by pressurizing the space between the housing and the flexible cylinder, thus causing the flexible cylinder to close by moving radially inwardly and de-pressurizing said space to open said valve, the fluid flow being controlled by an electrically operated valve;

purging said conduit and probe immediately prior to operating said valve by passing pressurized air in a reverse flow direction from a point immediately upstream of the valve through the conduit and probe and into the pipe.

9. The method of claim 8 including drawing the purged air from the same separate source as is used to operate the fluidly operated valve.

* * * * *